United States Patent [19]
Heinisch et al.

[11] Patent Number: 6,013,647
[45] Date of Patent: Jan. 11, 2000

[54] BENZOXAZINEDIONE DERIVATIVES, METHOD OF PRODUCING THEM AND USES THEREOF

[75] Inventors: Lothar Heinisch; Steffen Wittmann; Ute Moellmann, all of Jena; Rolf Reissbrodt, Wernigerode, all of Germany

[73] Assignee: Gruenenthal GmbH, Aachen, Germany

[21] Appl. No.: 09/035,344

[22] Filed: Mar. 5, 1998

[30] Foreign Application Priority Data

Mar. 5, 1997 [DE] Germany ............................ 197 08 846

[51] Int. Cl.[7] ...................... A61K 31/535; C07D 265/26
[52] U.S. Cl. .................. 514/230.5; 514/25; 514/152; 514/197; 514/198; 514/201; 514/202; 536/16.8; 540/217; 540/221; 540/222; 540/335; 540/336; 544/73; 544/93
[58] Field of Search ....................... 544/73, 93; 540/217, 540/222, 335, 336, 221; 514/152, 197, 202, 230.5, 201

[56] References Cited

U.S. PATENT DOCUMENTS

| | | | |
|---|---|---|---|
| 3,047,573 | 7/1962 | Takashi et al. | 544/93 |
| 4,338,436 | 7/1982 | Herron et al. | 540/215 |
| 4,338,439 | 7/1982 | Herron et al. | 540/224 |
| 5,292,735 | 3/1994 | Sugiomoto et al. | 514/230.5 |

FOREIGN PATENT DOCUMENTS

| | | |
|---|---|---|
| 0341948 | 11/1989 | European Pat. Off. . |
| 0472062 A1 | 2/1992 | European Pat. Off. . |
| 496332 | 7/1992 | European Pat. Off. . |
| 831710 | 1/1960 | France . |
| 1147583 | 4/1963 | Germany . |
| 27 38 631 | 3/1975 | Germany . |
| 878603 | 10/1961 | United Kingdom . |
| 97/49670 | 12/1993 | WIPO . |
| WO 93/25542 | 12/1993 | WIPO . |

OTHER PUBLICATIONS

Shapiro et al., "Pyridylethylated Benzoxazinediones", J.A.C.S. 79:2811–2814 (1957).

Vuettner et al., Chemical Abstracts, vol. 80, abstract 27280, 1974.

Yoshida et al., Chemical Abstracts, vol. 109, abstract 186898, 1988.

Abstract of GB 878,603 (counterpart of DE–AS–1,147,583, listed above) 1961.

Hantke et al., "Dihydroxybenzolyserine–a Siderophore for E. coli", FEMS Microbiology Letters, 67: 5–8 (1990).

Kanai et al., "Vanoxonin, A New Inhibitor of Thymidylate Synthetase", The Journal of Antibiotics, vol. XXXVIII, No. 1., pp. 39–50 (1985).

Corbin et al., "The Isolation and Identification of 2.3–Dihydroxybenzoic Acid and 2–N,6–N–Di (2,3–dihydroxybenzoyl)–L–lysine and Formed by Iron Deficient Azotobacter vinelandii", Biochemistry, 8(3):757–762 (1969).

McKee et al., "Iron Transport Mediated Drug Delivery Systems: Synthesis and Antibacterial Activity . . . ", Bioconjugate Chem., 2(4): 281–291 (1991).

Chimiak et al., "Lysine Analogues of Siderophores", Structure and Bonding, 58: 90–96 (1984).

Reissbrodt et al., "Growth Promotion of Synthetic Catecholate Derivatives on Gram–negative Bacteria", Biometals, 6: 155–162 (1993).

Arisawa et al., "In Vitro and In Vivo Evaluation of Ro 09–1428, A New Parenteral Cephalosporing with High Antipseudomonal Activity", Antimicrobial Agents and Chemotherapy, 35(4) : 653–659 (1991).

Movrin et al., "1,3–Benzoxazine–2,4–dione . . . ", Chemical Abstracts, No. 191020a, 105: 723 (1985).

Waisser et al., "Differences Between the Structure and Activity of Potentially Antimycobacterial . . . ", Chemical Abstracts, No. 237626w, 125 (19): 40 (1996).

(List continued on next page.)

Primary Examiner—Richard L. Raymond
Attorney, Agent, or Firm—Evenson, McKeown, Edwards & Lenahan, P.L.L.C.

[57] ABSTRACT

This invention relates to new benzoxazinedione derivatives corresponding to the formula I:

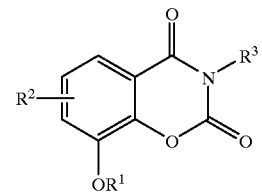

I wherein $R^1$=H or carboxyalkyl, $R^2$=H, alkyl or phenyl, and $R^3$ represents different acid groups derived from amino acids, dipeptides and hydrazones or conjugates thereof with active ingredients, e.g. antibiotics. The compounds may be present as free acids, in the form of their salts or as readily cleavable esters. The compounds according to the invention constitute heterocyclically protected catechol derivatives and are effective as siderophores against gram-negative bacterial strains, particularly against Pseudomonads and strains of E. coli and Salmonella. In the form of their conjugates with active ingredients, e.g. antibiotics (as "siderophore-antibiotic conjugates"), they can transport the latter into bacterial cells and can improve or extend the antibacterial effect thereof, sometimes even in relation to bacterial strains which are resistant to other β-lactams. In addition, said compounds, as potential prodrug forms for iron chelating agents, are suitable for use against diseases which are caused by a disorder of the iron metabolism. The invention can be employed in pharmaceutical research and in the pharmaceutical industry, and in agriculture.

25 Claims, No Drawings

OTHER PUBLICATIONS

Devaux et al., "Dihydrobenzoxaziones and –benzoxazinediones", *Chemical Abstracts*, No. 37526z, 81: 386 (1974).

Yoshida et al., "Benadrostin, New Inhibitor of Poly(ADP-Ribose) Synthetase, Produced by Actinomycetes", *The Journal of Antibiotics*, vol. XLI (8) : 1015–1018 (1988).

Herbert et al., "Biosynthesis of the Antibiotic Obafluorin from p–Aminophenylaline and Glycine (Glyoxylate)", *J. Chem. Soc. Perkin Trans.*, 1: 109–113 (1992).

Phillips et al., "Ring Opening of Cyclic Salicylamides", *Journal of Pharmaceutical Science*, 58(11) : 1514–1416 (1969).

Wagner et al, *Pharmazie,* (33)1:15–19 (1978).

Lespagnol et al., *Iron Transport in Microbes, Plants and Animals,* VCH Verlagsgesellschaft mbH, Weinheim (1987), pp. 179–185.

BENZOXAZINEDIONE DERIVATIVES, METHOD OF PRODUCING THEM AND USES THEREOF

FIELD OF THE INVENTION

The present invention relates to new benzoxazinedione derivatives, and to conjugates thereof with active ingredients, e.g. antibiotics. These compounds are effective as siderophores for gram-negative bacteria, i.e. they can supply bacteria with iron ions, and, in the form of their conjugates with active ingredients, e.g. with antibiotics (as "siderophore-antibiotic conjugates"), can transfer active ingredients into the bacterial cell via iron transport routes and can thereby improve and extend the efficacy thereof. These compounds thus make a contribution to the combatting of penetration-related resistance to antibiotics. The compounds according to the invention constitute precursors of iron chelating agents or heterocyclically protected catechol compounds, i.e. they can be converted enzymatically into corresponding catechol derivatives. They can influence the biological metabolism of iron and can thereby influence associated diseases in various ways. The area of application of the invention is pharmaceutical research and in the pharmaceutical industry. Benzoxazinedione derivatives of formula I which comprise the given substituents have not hitherto been described in the literature. In principle, the compounds constitute acylated catechol derivatives, one acyl component of which is bonded into a benzoxazine ring.

BACKGROUND OF THE INVENTION

It is known that certain catechol structures play an essential role as iron-complexing structural elements in natural siderophores ("Iron Transport in Microbes, Plants and Animals", Eds.: Winkelmann, G., van Helm, D., Neilands, J. B., V.Ch. Verlagsgesellschaft Weinheim, 1987), e.g. enterobactin, which is a siderophore for *E. coli* and other bacterial strains, is a trimer of N-(2,3-dihydroxybenzoyl)-L-serine. The monomer is also effective as a siderophore (Hantke, K., FEMS Microbiol. Lett. 67 (1990), 5).

N-(2,3-dihydroxybenzoyl)glycine has been found to be a siderophore for B. subtilis (Ito, T., Neilands, J. B., J. Amer. Chem. Soc. 80 (1958), 4645). Some catechol-substituted amino acid derivatives have already been produced synthetically, e.g. N-(2,3-dihydroxybenzoyl)-L-threonine (Kanai, F., Kaneko, T., Morishima, H., Isshiki, K., Taketa, T., Takeuchi, T., Umezawa, H., J. Antibiot. 38 (1985), 39), $N^2,N^6$-bis-(2,3-dihydroxybenzoyl)-L-lysine (Corbin, J. L., Bulen, W. A., Biochemistry 8 (1969), 757; McKee, J. A., Sharma, S. K., Miller, M. J., Bioconjugate Chem. 2 (1991) 281), and $N^2,N^6$-bis-(2,3-dihydroxybenzoyl)-lysyl-$N^6$-(2,3-dihydroxybenzoyl)lysine (Chimiak, A., Neilands, J. B., Structure and Bonding 58, (1984), 89). It is also known that certain glyoxylic acid benzhydrazones, oxanilic acid derivatives, etc., can serve as siderophores for different bacterial strains (Reissbrodt, R., Heinisch, L., Moellmann, U., Rabsch, W., Ulbricht, H., BioMetals 6 (1993), 155).

Various catechol compounds have been bonded to β-lactams, by means of which an increase in the antibacterial efficacy of these antibiotics has been achieved due to their transfer into the bacterial cell via bacterial transport routes for iron (e.g. Arisawa, M., Sekine, Y., Shimizu, S., Takano, H., Angehrn, P., Then, R. L., Antimicrob. Agents Chemother. 35 (1991), 653). However, no compounds of this type have hitherto achieved their ultimate purpose of clinical application. The achievement of this object necessitates a search for new synthetic siderophores which are suitable for forming conjugates with antibiotics.

Secondly, as chelating agents for iron, siderophores are potentially capable of influencing the biological metabolism of iron, and of diseases associated therewith, in various ways. Thus the siderophore desferrioxamine B (desferal) has been successfully used in diseases which are caused by an excess of iron (e.g. thalassaemia).

Benzoxazinedione derivatives are known which have no substituent in the 8-position and which are not derived from catechol, e.g. 3-carboxymethyl-2,4-dioxobenzoxazine (e.g. Lespagnol, A., Lespagnol, Ch., Bernier, J. L., Cazin, J. C., Cazin, M., Bull. Soc. Pharm. Lille 4, (1972), 179–185). The preparation of benzoxazinedione derivatives from acyloxybenzoyl chloride and amine components with the elimination of HCl and methanol has not been described previously.

SUMMARY OF THE INVENTION

The present invention serves for the identification of new benzoxazinedione derivatives and to the use thereof. The aim of the invention is to develop suitable compounds for the transfer of active ingredients, e.g. antibiotics, into the bacterial cell via bacterial transport routes for iron. The aim is secondly to identify, with these compounds, new precursors or prodrug forms for chelating agents for iron, which can influence the biological metabolism of iron in various ways and can thereby influence diseases associated therewith. The aim of bonding the catechol structure into the heterocyclic benzoxazinedione structure is that the compounds in their acylated form, and particularly the conjugates thereof with antibiotics, should exhibit improved pharmacological properties compared with free catechols or can be employed as pharmacological forms of transport for the actual penetration-promoting catechol compounds.

The underlying object of the present invention is to provide new benzoxazinedione derivatives which can function as siderophores or as biological chelating agents for iron.

This object is achieved according to the invention by the provision of new benzoxazinedione derivatives of general formula I

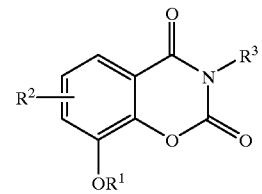

wherein $R^1$=H, CO-alkyl or COO-alkyl, $R^2$=H, alkyl or halogen, where the alkyl groups may be straight chain or branched and contain 1 to 8 carbon atoms, preferably 1 to 5 carbon atoms, and $R^3$ represents the following substituents:

a) $R^3$=—Z—$CHR^4$—$COR^5$ with Z =

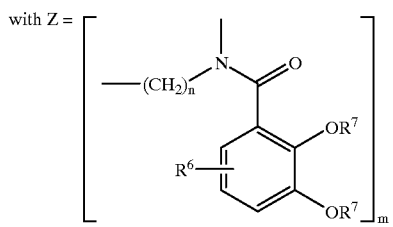

with $R^4$=H. $C_{1-8}$alkyl, phenyl or substituted phenyl, particularly hydroxy- or acyloxy-phenyl, or with $R^4$=$(CH_2)_n COX$ with X=OA, wherein A=H. $C_{1-8}$ straight or branched alkyl, benzyl, an alkali metal ion or an ammonium ion or a substituted ammonium ion, or with X=an active ingredient residue, particularly a residue of an antibiotic, which is bonded via an OH or an NH group, and with n=1–10, or with $R^4$=$(CH_2)_n$—Y, wherein Y represents a benzoxazinedione residue of the formula

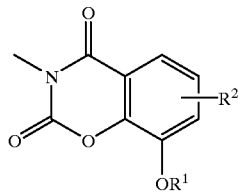

wherein $R^1$ and $R^2$ are as defined above, both benzoxazinedione residues may be the same or different, and n=1–10, and with $R^5$=OA, wherein A is defined as above, or with $R^5$=an active ingredient residue, particularly a residue of an antibiotic, which is bonded via an OH or an NH group, or with $R^5$=NH—$CHR^8$—$COR^9$, with $R^8$=H, $C_{1-8}$ straight or branched alkyl, phenyl or substituted phenyl, and with $R^9$=OA, wherein A is as defined above, or with $R^9$=an active ingredient residue, particularly a residue of an antibiotic, which is bonded via an OH or an NH group, or with $R^5$ =

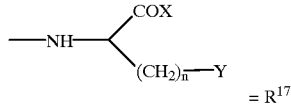

with X and Y as above, and n=1–10, and with $R^6$=H, $C_{1-8}$ straight or branched alkyl, or halogen, and with $R^7$=H, CO—$C_{1-6}$alkyl or COO—$C_{1-6}$alkyl, and n=1–10 and m=1–2, or b) $R^3$=$CHR^4$—$COR^5$, with $R^4$ and $R^5$ as above, or c) $R^3$ =

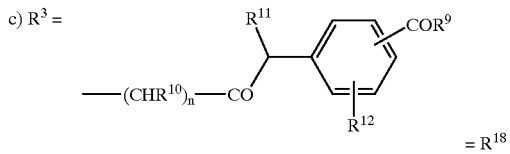

with $R^{10}$ and/or $R^{11}$=H, $C_{1-8}$ straight or branched alkyl, phenyl or substituted phenyl, n=1–10, and with $COR^9$ and $R^{12}$ in all possible positions, $R^9$ as defined above, and $R^{12}$=H, $C_{1-8}$ straight or branched alkyl, halogen, hydroxy, $C_{1-8}$ straight or branched alkoxy, a benzoxazinedione residue Y, or $R^{12}$ =

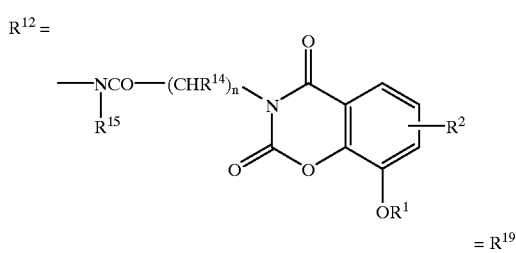

with $R^1$, $R^2$ as above, $R^{14}$, $R^{15}$ as $R^1$, $R^2$, and where n=1–10, or d) $R^3$ =

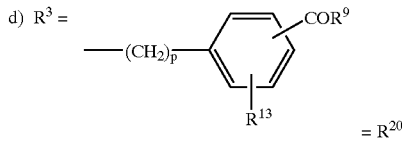

with $R^{13}$ and $COR^9$ in all possible positions and with $R^{13}$=H, $C_{1-8}$ straight or branched alkyl, halogen, hydroxy, $C_{1-8}$ straight or branched alkoxy or a benzoxazinedione residue Y, and with $R^9$ as above and p=0–2, or e)

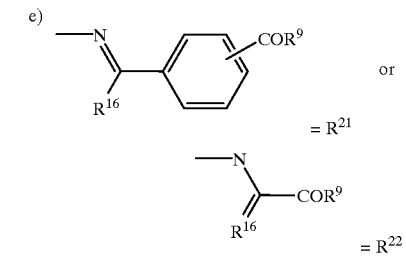

with $R^9$ as above, $R^6$=H, $C_{1-8}$ straight or branched alkyl, phenyl or substituted phenyl, or f) $R^3$=an active ingredient residue, particularly a residue of an antibiotic, which is bonded via an OH group or an NH group.

DETAILED DESCRIPTION OF PREFERRED EMBODIMENTS

In the above formulas and hereinafter, the term "acyl" denotes a straight chain or branched $C_1$ to $C_6$ alkanoyl or a straight chain or branched $C_1$ to $C_6$ alkoxycarbonyl, preferably a $C_1$ to $C_5$ alkanoyl or alkoxycarbonyl in particular. A straight chain or branched alkyl and a straight chain or branched alkoxy, also in compound words such as a straight chain or branched alkoxyalkyl or acyloxyalkyl, denote a straight chain or branched $C_1$ to $C_8$ alkyl or $C_1$ to $C_8$ alkoxy, preferably a $C_1$ to $C_5$ alkyl or $C_1$ to $C_1$ alkoxy in particular. A substituted phenyl denotes a phenyl which is substituted by a straight chain or branched $C_{1-8}$alkyl, or by a halogen, particularly Cl or F, or by a straight chain or branched $C_{1-8}$alkoxy, hydroxy, carboxy, phenyl, amino, $C_{1-5}$alkylamino, di-$C_{1-5}$alkylamino, a straight chain or branched $C_{1-8}$alkoxycarbonyl, $C_{1-5}$acyloxy, or a halogen-substituted $C_{1-8}$alkyl. A substituted ammonium ion is an ammonium ion which is multiply- or singly-substituted, such as one to four times, by an alkyl, for example. An alkali metal ion may be a sodium or potassium ion, for example.

The term "active ingredient residue" denotes the residue of any suitable antibacterial active ingredient comprising a free NH or OH group, wherein the active ingredient is esterified or converted to an amide with the compound of formula I via this NH or OH group. The bond between the catechol derivative and the antibiotic can be formed either directly or via customary linker groups, e.g. aminocarboxylic acids, hydroxycarboxylic acids, diamines or diols. The term "antibiotic" is to be understood, for example, as a corresponding β-lactam containing an NH or OH group, e.g. a cephalosporin, e.g. cephalexin, cephadroxil or claforan, or a penicillin, e.g. ampicillin, amoxicillin or an O-acyl-amoxicillin derivative, or a tetracycline derivative, e.g. an aminodioxycycline, or an antibiotic of the aminoglycoside, macrolide, quinolone or carbapenem type.

If asymmetric carbon atoms are present, the invention likewise relates to the corresponding D- and L- forms, enantiomers and diastereomers, and to racemates and mixtures of enantiomers and diastereomers.

The compounds may exist as free acids, in the form of their salts or as readily cleavable esters, such as esters which can be cleaved under physiological conditions.

The compounds of formula I in which $R^5$ or $R^9$=OH which are provided according to the invention are prepared by he condensation of 2,3-diacyloxybenzoyl chloride with corresponding amino components, e.g. amino acids, dipeptides or aminobenzoic acids, in sodium bicarbonate solution according to the following reaction scheme 1:

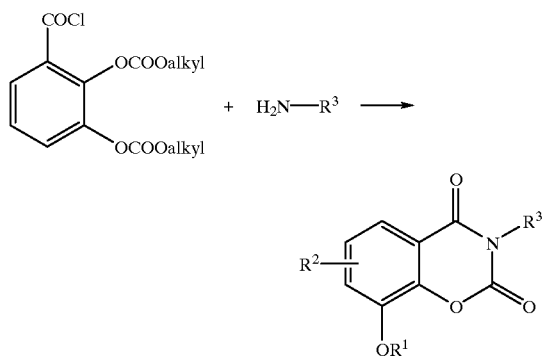

where $R^1$=COO-alkyl or H.
Reaction scheme 1:

In the course of the reaction, the COO-alkyl group on $R^1$ can be cleaved hydrolytically, so that compounds with $R^1$=H can be formed. These can be re-acylated, e.g. to form compounds with $R^1$=CO-alkyl.

Compounds of formula I with $R^5$ or $R^9$=OH can also be prepared, by the same principle, according to reaction scheme 2, by the reaction of corresponding amide derivatives, e.g. 2,3-dihydroxybenzhydrazones, with alkyl esters of chloroformic acid in alkaline medium.

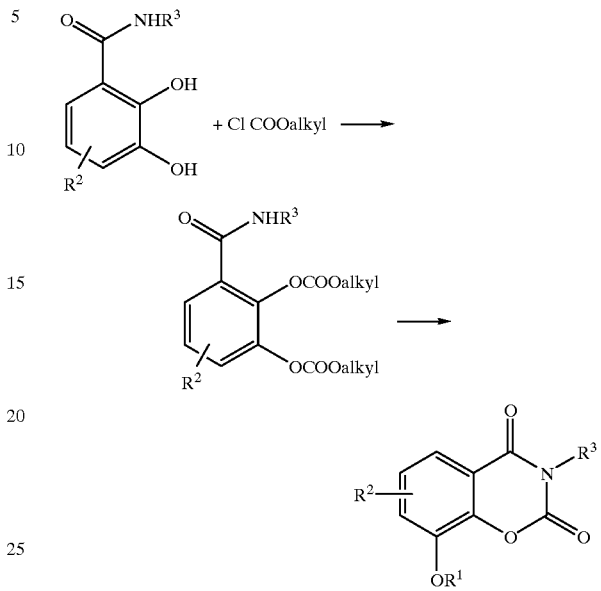

Reaction scheme 2:

The compounds according to the invention of formula I in which $R^3$, $R^5$, $R^9$ or X=an active ingredient residue, e.g. the residue of an antibiotic, are prepared as follows, for example:

(a) by first preparing the corresponding chloride from a compound of formula I with A=H by customary methods, e.g. by means of phosphorus pentachloride in carbon tetrachloride, and then reacting this chloride, in a suitable solvent e.g. tetrahydrofuran, with an active ingredient or antibiotic which contains a free OH or NH group and optionally a customary linker group also, such as residues of a diaminocarboxylic acid, of a hydroxycarboxylic acid or of a diamine or diol for example, or (b) by reacting a compound of formula I with A=H, e.g. by the mixed anhydride method, firstly with chloroformic acid ester and a tertiary amine, e.g. triethylamine, and then with the corresponding active ingredient, which contains a free OH or NH group and optionally a customary linker group also, such as residues of a diaminocarboxylic acid, of a hydroxycarboxylic acid or of a diamine or diol for example, together with a suitable tertiary amine, e.g. triethylamine, in a suitable solvent e.g. tetrahydrofuran.

The compounds of formula I which contain a carboxyl group may be present as free acids, in the form of their salts, or as readily cleavable esters, particularly as esters which are cleavable under physiological conditions. The compounds are purified by customary methods known from the prior art, for example by recrystallization or by means of chromatographic methods.

The compounds of formula I according to the invention, particularly the compounds without an active ingredient residue, are effective as siderophores for various gram-negative strains of bacteria. Consequently, these compounds can be employed as growth factors for certain bacterial cultures.

Testing for siderophore efficacy according to German Industrial Standard DIN 58 940 was performed using various bacterial indicator mutants which exhibit reduced growth under the test conditions due to a lack of their own iron transport systems. The promotion of growth can be ascertained after the addition of the test substances as external siderophores. In the indicator mutants, the synthesis of the respective siderophores, e.g. pyoverdin, pyochelin, enterobactin, aerobactin or yersiniabactin, or the biosynthesis of aromatic compounds, is blocked, or there is a lack of receptors for enterobactin, pyochelin or pyoverdin and for other important components for the bacterial transport of iron (e.g. the membrane proteins Cir, Fiu, FepA and the TonB protein also). Under conditions where there is a lack of iron, these mutants therefore cannot grow or can only grow in a very retarded manner. In particular, the following indicator mutants were used: *Pseudomonas aeruginosa* PAO 6609, K 407, *E. coli* AB 2847, *Salmonella typhimurium* enb-7, TA 2700, and *Yersinia enterocolitica* WAH 5030. The controls used were ferrioxamine E for the Pseudomonas strains, ferrioxamine G for the Salmonella strains, and ferrichrome for the *E. coli* strains. The test substances were each employed in an amount of 5 μg/test plate.

The growth areas of the indicator mutants (diameter in mm) under the effect of the test substances are given in Table 1.

TABLE 1

Growth areas (in mm) of siderophore indicator strains with selected benzoxazinedione derivatives

| Substance No. | *Pseud. aeiuginosa* PAO 6609 | *Y. enterocol.* WAH 5030 | *E. coli* AB 2847 | Salmonella enb-7 | Salmonella TA 2700 |
|---|---|---|---|---|---|
| 1 | 0 | | 15 | 18 | 13 |
| 2 | 13 | | 10 | 22 | 21 |
| 4 | 0 | | 0 | 14 | 0 |
| 7 | 0 | | 0 | 10 | 0 |
| 9 | 0 | 20 | 24 | 0 | 16 |
| control | a) 35 | a) 40 | b) 23 | c) 38 | c) 20 | a) ferrioxamine E, b) ferrichrome, c) ferrioxamine G

Due to their properties as bacterial siderophores, the compounds of general formula I can serve as transport vehicles or penetration accelerators for antimicrobial antibiotics and other active ingredients, i.e. in conjugates with antibiotics or other active ingredients they can serve to transport the latter into the microbial cell via iron transport routes and can thus increase the efficacy thereof. Consequently, compounds of general formula I where $R^3$, $R^5$, $R^9$ or X is an active ingredient residue, particularly a β-lactam, possess an antibacterial efficacy, even against bacteria which are resistant to other β-lactams, wherein the existing siderophore effect of the benzoxazinedione residue is combined with the antibacterial effect of the molecule as a whole. In order to determine antibacterial efficacy, the minimum inhibiting concentrations (MIC) were determined according to DIN 58 940 for the following bacterial strains: *Pseudomonas aeruginosa* SG 137, NCTC 10662, ATCC 27853, *E. coli* ATCC 25922, *Klebsiella pneumoniae* ATCC 10031, *Stenotrophomonas maltophilia* GN 12873, and *Staphylococcus aureus* SG 511. The results of the test are given in Table 2. As shown by the results, the compounds tested exhibited a high antibacterial efficacy, which in part surpassed that of the comparison substances azlocillin and ampicillin. The dependence of the antibacterial effect on the bacterial transport of iron was demonstrated by varying the iron content of the test medium and by the use of iron transport mutants.

Due to their properties as siderophores or as chelating agents for iron, compounds of general formula I, particularly those compounds without an active ingredient residue, as well as the salts thereof when acidic groups are present and as well as esters which are cleavable under physiological conditions, are suitable for use as drugs for diseases which are caused by a disorder of the physiological metabolism of iron. On account of their antibacterial efficacy, compounds of general formula I with $R^3$, $R^5$, $R^9$ or X=an active ingredient residue, e.g. the residue of an antibiotic containing an NH or OH group, as well as the salts thereof when acidic groups are present and as well as esters which are cleavable under physiological conditions, are suitable for use as drugs for bacterial infections in humans and working animals.

The compounds of formula I can be employed against said diseases either on their own or in the form of pharmaceutical preparations with physiologically compatible adjuvant or supporting substances which are known from the prior art, wherein all customary pharmacological forms of application are possible in principle.

EXAMPLES

Example 1

Preparation of (8-methoxycarbonyloxy-2,4-dioxobenzoxazin-3-yl)-acetic acid (formula I with $R^1$=COOCH$_3$, $R^2$=H, $R^3$=CH$_2$COOH).

A solution of 2.75 g glycine in 175 ml 0.5 M sodium hydrogen carbonate solution was cooled to 0–5° C. in an ultrasonic bath. 10.5 g 2,3-di-(methoxycarbonyloxy)-benzoyl chloride, dissolved in 20 ml absolute tetrahydrofuran, was added drop-wise at 0–5° C. with stirring. The turbid solution which had formed after 1 hour was filtered and the tetrahydrofuran was distilled off. The substance obtained was filtered out under suction and was washed with a little cold water. For its purification, the substance was re-dissolved in 0.5 M sodium hydrogen carbonate solution, filtered, and precipitated with concentrated hydrochloric acid. Colorless crystals, which had a melting point of 205–208° C., were obtained in a yield of 70% of theoretical.

Example 2

Preparation of (8-methoxycarbonyloxy-2,4-dioxobenzoxazin-3-yl)-acetyl-glycine (formula I with $R^1$=COOCH$_3$, $R^2$=H, $R^3$=CH$_2$CONHCH$_2$COOH).

This compound was prepared, analogously to example 1, from glycylglycine and 2,3-di-(methoxycarbonyloxy)-benzoyl chloride in aqueous sodium bicarbonate solution. After recrystallization from water, colorless crystals with a melting point of 195–198° C. were obtained in a yield of 70% of theoretical.

Example 3

Preparation of (8-methoxycarbonyloxy-2,4-dioxobenzoxazin-3-yl)-acetyl-L-alanine (formula I with $R^1$=COOCH$_3$, $R^2$=H, $R^3$=CH$_2$CONH—CH(CH$_3$)—COOH).

This compound was prepared, analogously to example 1, from glycyl-L-alanine and 2,3-di-(methoxycarbonyloxy)-benzoyl chloride in aqueous sodium bicarbonate solution. After recrystallization from ethyl acetate, colorless crystals with a melting point of 180–185° C. were obtained in a yield of 70% of theoretical.

Example 4

Preparation of (8-hydroxy-2,4-dioxobenzoxazin-3-yl)-acetyl-L-alanine (formula I with $R^1$=H, $R^2$=H, $R^3$=CH$_2$CONH—CH(CH$_3$)—COOH).

9

This compound could be recovered by preparative HPLC (elutant: 1/1 acetonitrile/water containing 0.05% trifluoroacetic acid) from the mother liquor arising during the isolation of (8-methoxycarbonyloxy-2,4-dioxobenzoxazin-3-yl)-acetyl-L-alanine (product from example 3). After recrystallization from ethyl acetate, colorless crystals with a melting point of 203–204° C. were obtained in a yield of 20% of theoretical.

Example 5
Preparation of (8-methoxycarbonyloxy-2,4-dioxobenzoxazin-3-yl)-acetyl-L-leucine (formula I with $R^1$=COOCH$_3$, $R^2$=H, $R^3$=CH$_2$CONH—CH(COOH)—CH$_2$CH(CH$_3$)$_2$).

This compound was prepared, analogously to example 1, from glycylleucine and 2,3-di-(methoxycarbonyloxy)-benzoyl chloride in aqueous sodium bicarbonate solution. It was isolated by the immediate extraction, with ethyl acetate, of the mixture obtained after acidification with hydrochloric acid, repeatedly washing the resulting solution with water, drying over sodium sulfate and removing the solvent under vacuum. After preparative HPLC (elutant: 1/1 acetonitrile/water containing 0.05% trifluoroacetic acid) and recrystallization from water, colorless crystals with a melting point of 179–181° C. were obtained in a yield of 60% of theoretical.

Example 6
Preparation of (8-hydroxy-2,4-dioxobenzoxazin-3-yl)-acetyl-L-leucine (formula I with $R^1$=H, $R^2$=H, $R^3$=CH$_2$CONH—CH(COOH)—CH$_2$CH(CH$_3$)$_2$).

This compound was isolated by means of preparative HPLC (elutant: 1/1 acetonitrile/water containing 0.05% trifluoroacetic acid) as a second product from the reaction mixture obtained on the preparation of (8-methoxycarbonyloxy-2,4-dioxobenzoxazin-3-yl)-acetyl-L-leucine (the product from example 5). After recrystallization from ethyl acetate, colorless crystals with a melting point of 204–207° C. were obtained in a yield of 25% of theoretical.

Example 7
Preparation of 2-L-(8-methoxycarbonyloxy-2,4-dioxobenzoxazin-3-yl)-propionic acid (formula I with $R^1$=COOCH$_3$, $R^2$=H, $R^3$=CH(CH$_3$)—COOH).

This compound was prepared, analogously to example 4, from L-Alanine and 2,3-di-(methoxycarbonyloxy)-benzoyl chloride in aqueous sodium bicarbonate solution. After preparative HPLC (elutant: 2/3 acetonitrile/water containing 0.05% trifluoroacetic acid), a colorless foam was obtained in a yield of 50% of theoretical.

Example 8
Preparation of L-(8-methoxycarbonyloxy-2,4-dioxobenzoxazin-3-yl)-phenylacetic acid (formula I with $R^1$=COOCH$_3$, $R^2$=H, $R^3$=C$_6$H$_5$—CH—COOH).

This compound was prepared, analogously to example 4, from L-phenylalanine and 2,3-di-(methoxycarbonyloxy)-benzoyl chloride in aqueous sodium bicarbonate solution. After preparative HPLC (elutant: 1/1 acetonitrile/water containing 0.05% trifluoroacetic acid) and recrystallization from water, colorless crystals with a melting point of 182–184° C. were obtained in a yield of 50% of theoretical.

Example 9
Preparation of 4-[(8-methoxycarbonyloxy-2,4-dioxobenzoxazin-3-yl-imino)-methyl]-benzoic acid (formula I with $R^1$=COOCH$_3$, $R^2$=H, $R^3$=—N=CH—C$_6$H$_4$—COOH(p).

10

2 ml methyl chloroformate were added at 0° C., with stirring, to a solution of 0.3 g 4-[(2,3-dihydroxybenzoyl)-hydrazonomethyl)]-benzoic acid in 2 ml of 2 N aqueous sodium hydroxide solution. The mixture was stirred for 30 minutes and was then acidified with hydrochloric acid. The crude product was dissolved in hot dimethylformamide, the solution was filtered, and the product was re-precipitated with water. Further purification was effected by means of preparative HPLC (elutant: 1/1 acetonitrile/water containing 0.05% trifluoroacetic acid). Colorless crystals with a melting point of 232–234° C. were obtained.

Example 10
Preparation of N-[(8-methoxycarbonyloxy-2,4-dioxobenzoxazin-3-yl)-acetyl]-ampicillin (formula I with $R^1$=COOCH$_3$, $R^2$=H, $R^3$=CH$_2$—CO—R$^5$, $R^5$=N-ampicillino-).

(a) Preparation of (8-methoxycarbonyloxy-2,4-dioxobenzoxazin-3-yl)-acetyl chloride.

A mixture of 1.07 g (3 mmoles) 8-methoxycarbonyloxy-2,4-dioxobenzoxazin-3-yl-acetic acid (substance 1) and 1 g phosphorus pentachloride in 5 ml of absolute carbon tetrachloride was carefully heated until the evolution of HCl was complete (30 minutes). The resulting solution was filtered and the filtrate was concentrated by evaporation. The residue was re-dissolved in hot carbon tetrachloride, and the acid chloride was precipitated with anhydrous petroleum ether and dried under high vacuum. 0.81 g of product (86% of theoretical) with a melting point of 80–82° C. were thus obtained.

(b) A solution of 0.78 g of the sodium salt of ampicillin in 12 ml of 80% tetrahydrofuran was cooled to −5° C. 0.63 g 8-methoxycarbonyloxy-2,4-dioxobenzoxazin-3-yl-acetyl chloride was added thereto in portions, with stirring. The mixture was stirred for 1 hour at 0C and for 1 hour at 20° C., and was then concentrated by evaporation under vacuum. The residue was treated with 50 ml water and 50 ml ethyl acetate. It was then slightly acidified (pH 3) with 1 M hydrochloric acid and was washed three times with aqueous sodium chloride solution. The organic phase was separated, dried over sodium sulfate and concentrated to a volume of 20 ml. The residue was treated with petroleum ether, whereupon 0.92 g (74% of theoretical) of the ampicillin derivative were obtained as a white powder.

Example 11
Preparation of N-(8-methoxycarbonyloxy-2,4-dioxobenzoxazin-3-yl)-acetyl]-amoxicillin (formula I with $R^1$=COOCH$_3$, $R^2$=H, $R^3$=CH$_2$COR$^5$, $R^5$=N-amoxicillino-).

A solution of 0.55 g amoxicillin in 8 ml of 80% tetrahydrofuran was treated with 0.22 ml triethylamine and cooled to −5° C. 0.45 g (8-methoxycarbonyloxy-2,4-dioxobenzoxazin-3-yl)-acetyl chloride (prepared as in example 8) was added thereto in portions, with stirring. The mixture was stirred for 1 hour at 0° C. and for 1 hour at 20° C. and was then concentrated by evaporation under vacuum. The residue was treated with 40 ml water and 40 ml ethyl acetate. It was slightly acidified (pH 3) with 1 M hydrochloric acid, shaken, and was washed with aqueous sodium chloride solution until free from acid. The separated organic phase was dried over sodium sulfate, extensively concentrated by evaporation and treated with petroleum ether. The amoxicillin derivative was thereupon precipitated as a white powder, in a yield of 80% of theoretical.

Example 12
Preparation of N-[(8-methoxycarbonyloxy-2,4-dioxobenzoxazin-3-yl)-acetyl-glycyl]-ampicillin (formula I with $R^1$=COOCH$_3$, $R^2$=H, $R^3$=CH$_2$—CO—NH—CH$_2$—COR$^5$, $R^5$=N-ampicillino-).

0.352 g (8-methoxycarbonyloxy-2,4-dioxobenzoxazin-3-yl)-acetyl-glycine (see example 2 for the preparation thereof), 140 μl triethylamine and a catalytic amount of dimethylaminopyridine were dissolved in 5 ml of absolute tetrahydrofuran and the solution was treated at −20° C. with 126 μl isobutyl chloroformate, with stirring. The mixture was stirred for 30 minutes at −20° C. 0.357 g of the sodium salt of ampicillin in 5 ml of 80% tetrahydrofuran were then added. The mixture was stirred for 1 hour at −20° C. and for 1 hour at +20° C., and was then concentrated by evaporation under vacuum. The residue was treated with ethyl acetate and water and was carefully acidified with 1 M hydrochloric acid. The organic phase was separated, washed three times with sodium chloride solution, dried over sodium sulfate, and partially concentrated by evaporation. The ampicillin derivative was precipitated by adding petroleum ether, and was purified by means of preparative HPLC (elutant: 1/1 acetonitrile/ water containing 0.05% trifluoroacetic acid).

Example 13
Preparation of N-[(8-methoxycarbonyloxy-2,4-dioxobenzoxazin-3-yl)-acetyl-L-alanyl]-ampicillin (formula I with $R^1$=COOCH$_3$, $R^2$=H, $R^3$=CH$_2$—CONH—CH(CH$_3$)—COR$^5$, $R^5$=N-ampicillino-).

This compound was prepared, analogously to example 12, from (8-methoxycarbonyloxy-2,4-dioxobenzoxazin-3-yl)-acetyl-L-alanine (see example 3 for the preparation thereof) and the sodium salt of ampicillin. Purification was effected by means of preparative HPLC (elutant: 1/1 acetonitrile/ water containing 0.05% trifluoroacetic acid), whereupon a colorless solid was obtained in a yield of 65% of theoretical.

Example 14
Preparation of N-[(8-methoxycarbonyloxy-2,4-dioxobenzoxazin-3-yl)-acetyl-L-leucyl-ampicillin (formula I with $R^1$=COOCH$_3$, $R^2$=H, $R^3$=CH$_2$—CONH—CH(COR$^5$)—CH$_2$CH(CH$_3$)$_2$, $R^5$ =N-ampicillino-).

This compound was prepared, analogously to example 12, from (8-methoxycarbonyloxy-2,4-dioxobenzoxazin-3-yl)-acetyl-L-leucine (see example 5 for the preparation thereof) and the sodium salt of ampicillin. Purification was effected by means of preparative HPLC (elutant: 2/3 acetonitrile/ water containing 0.05% trifluoroacetic acid), whereupon a colorless solid was obtained in a yield of 60% of theoretical.

Example 15
Preparation of N-[(8-methoxycarbonyloxy-2,4-dioxobenzoxazin-3-yl)-acetyl]-O-n-propionyl-amoxicillin (formula I with $R^1$=COOCH$_3$, $R^2$=H, $R^3$=CH$_2$COR$^5$, $R^5$=N-(O-n-propionyl)-amoxicillino-).

0.385 g N-[(8-methoxycarbonyloxy-2,4-dioxobenzoxazin-3-yl)-acetyl]-amoxicillin (see example 11 for the preparation thereof) was dissolved in 25 ml tetrahydrofuran and the solution was cooled to −78° C. 0.34 ml triethylamine, followed by 0.16 ml propionyl chloride, were added with stirring. The reaction mixture was stirred for 30 minutes at −60° C. and for 1 hour at 20° C. Thereafter, it was concentrated by evaporation under vacuum, and the residue was treated with water and ethyl acetate. After acidification with 1 M hydrochloric acid (pH 3), the mixture was washed with aqueous sodium chloride solution until free from acid. The separated organic phase was dried over sodium sulfate, extensively concentrated by evaporation, and treated with petroleum ether. The amoxicillin derivative was thereby precipitated as a white powder in a yield of 40% of theoretical.

Example 16
Preparation of 4-(8-methoxycarbonyloxy-2,4-dioxobenzoxazin-3-yl)-benzoic acid (formula I with $R^1$=COOCH$_3$, $R^2$=H, $R^3$=C$_6$H$_4$-COOH (p)).

This compound was prepared, analogously to example 1, from 4-aminobenzoic acid and 2,3-di-(methoxycarbonyloxy)-benzoyl chloride in aqueous sodium hydrogen carbonate solution. After recrystallization from ethyl acetate, colorless crystals with a melting point of 236–240° C. were obtained in a yield of 80% of theoretical.

Example 17
Preparation of 2L, 6-bis(8-methoxycarbonyloxy-2,4-dioxo-1,3-benzoxazin-3-yl)-hexanoic acid (formula I with $R^1$=COOCH$_3$, $R^2$=H, $R^3$=CHR$^4$—COOH, $R^4$=(CH$_2$)$_4$Y).

This compound was obtained, analogously to example 5, as a colorless foam from L-lysine and 2 molar equivalents of 2,3-di-(methoxycarbonyloxy)-benzoyl chloride in aqueous sodium hydrogen carbonate solution.

Example 18
Preparation of the sodium salt of N-[4-(8-methoxycarbonyloxy-2,4-dioxo-1 3-benzoxazin-3-yl)-benzoyl]-ampicillin (formula I with $R^1$=COOCH$_3$, $R^2$=H, $R^3$=R$^{20}$ with $R^{13}$=H, COR$^9$ in the 4-position, $R^9$=N-ampicillino (Na salt), p=0).

(a) Preparation of 4-(8-methoxycarbonyloxy-2,4-dioxo-1,3-benzoxazin-3-yl)-benzoyl chloride.

This compound was prepared, analogously to substance 10a, from substance 16 and phosphorus pentachloride in carbon tetrachloride. A colorless oil was obtained in a yield of 65% of theoretical.

(b) Preparation of N-[4-(8-methoxycarbonyloxy-2,4-dioxo-1,3-benzoxazin-3-yl)-benzoyl-ampicillin.

This compound was prepared, analogously to substance 10b, from 4-(8-methoxycarbonyloxy-2,4-dioxo-1,3-benzoxazin-3-yl)-benzoyl chloride and the sodium salt of ampicillin. A white powder was obtained in a yield of 85% of theoretical.

(c) Sodium salt.

A solution of 0.25 g N-4-(8-methoxycarbonyloxy-2,4-dioxo-1,3-benzoxazin-3-yl)-benzoyl]-ampicillin in ethyl acetate was treated, while being cooled in ice and stirred, with a solution of 0.083 g sodium 2-ethylhexanoate in ethyl acetate. The product was precipitated with petroleum ether and filtered out. Purification was effected by means of preparative HPLC (elutant: acetonitrile/water). A white powder was thereby obtained in a yield of 0.202 g (79% of theoretical).

Example 19
Preparation of 4-(8-methoxycarbonyloxy-2,4-dioxo-1,3-benzoxazin-3-yl-methyl)-benzoic acid (formula I with $R^1$=COOCH$_3$, $R^2$=H, $R^3$=R$^{20}$ with $R^{13}$=H, COR$^9$ in the 4-position, $R^9$=OH, p=1).

This compound was prepared, analogously to substance 5, from 4-(aminomethyl)-benzoic acid and 2,3-di-(methoxycarbonyloxy)-benzoyl chloride in aqueous sodium hydrogen carbonate solution. After recrystallization from ethyl acetate, colorless crystals with a melting point of 220–222° C. were obtained in a yield of 65% of theoretical.

Example 20
Preparation of the sodium salt of N-[4-(8-methoxycarbonyloxy-2,4-dioxo-1,3-benzoxazin-3-yl-methyl)-benzoyl]-ampicillin (formula 1 with $R^1$=COOCH$_3$, $R^2$=H, $R^3$=R$^{20}$ with $R^{13}$=H, COR$^9$ in the 4-position, $R^9$=N-ampicillino (Na salt), p=1).

(a) Preparation of 4-(8-methoxycarbonyloxy-2,4-dioxo-1,3-benzoxazin-3-yl-methyl)-benzoyl chloride.

This compound was prepared, analogously to substance 10a, from substance 19 and phosphorus pentachloride in carbon tetrachloride. A colorless oil was obtained in a yield of 95% of theoretical.

(b) Preparation of N-[4-(8-methoxycarbonyloxy-2,4-dioxo-1,3-benzoxazin-3-yl-methyl)-benzoyl]-ampicillin.

This compound was prepared, analogously to substance 10b, from 4-(8-methoxycarbonyloxy-2,4-dioxo-1,3-benzoxazin-3-yl-methyl)-benzoyl chloride and the sodium salt of ampicillin. A white powder was obtained in a yield of 80% of theoretical.

(c) Sodium salt.

Preparation was effected, analogously to substance 18, from N-[4-(8-methoxycarbonyloxy-2,4-dioxo-1,3-benzoxazin-3-yl-methyl)-benzoyl]-ampicillin and sodium 2-ethylhexanoate in ethyl acetate. A white powder was obtained in a yield of 60% of theoretical.

Example 21

Preparation of 3,5-bis-(8-methoxycarbonyloxy-2,4-dioxo-1,3-benzoxazin-3-yl)-benzoic acid (formula I with $R^1$=COOCH$_3$, $R^2$=H, $R^3$=$R^{20}$ with $R^{13}$=Y in the 3-position, COR$^9$ in the 5-position, $R^9$=OH, p=0, $R^1$, $R^2$ as above).

This compound was prepared, analogously to substance 5, from 3,5-diaminobenzoic acid and 2 molar equivalents of 2,3-di-(methoxycarbonyloxy)-benzoyl chloride in aqueous sodium hydrogen carbonate solution. After recrystallization from ethyl acetate, colorless crystals with a melting point of 164–166° C. were obtained in a yield of 65% of theoretical.

Example 22

Preparation of the sodium salt of N-[3,5-bis-(8-methoxycarbonyloxy-2,4-dioxo-1,3-benzoxazin-3-yl)-benzoyl]-ampicillin (formula 1 with $R^1$=COOCH$_3$, $R^2$=H, $R^3$=$R^{20}$ with $R^{13}$=Y in the 3-position, COR$^9$ in the 5-position, $R^9$=N-ampicillino (Na salt), p=0, $R^1$, $R^2$ as above).

(a) Preparation of 3,5-bis-(8-methoxycarbonyloxy-2,4-dioxo-1,3-benzoxazin-3-yl)-benzoyl chloride.

This compound was prepared, analogously to substance 10a, from substance 21 and phosphorus pentachloride in carbon tetrachloride. It was obtained as a colorless foam in a yield of 90% of theoretical.

(b) Preparation of N-[3,5-bis-(8-methoxycarbonyloxy-2,4-dioxo-1,3-benzoxazin-3-yl)-benzoyl]-ampicillin.

This compound was prepared, analogously to substance 10b, from 3,5-bis-(8-methoxycarbonyloxy-2,4-dioxo-1,3-benzoxazin-3-yl)-benzoyl chloride and the sodium salt of ampicillin. It was obtained as a white powder in a yield of 80% of theoretical.

(c) Sodium salt.

This compound was prepared, analogously to substance 18, from N-[3,5-bis-(8-methoxycarbonyloxy-2,4-dioxo-1,3-benzoxazin-3-yl)-benzoyl]-ampicillin and sodium 2-ethylhexanoate in ethyl acetate. A white powder was obtained in a yield of 40% of theoretical.

Example 23

Preparation of 3-(8-methoxycarbonyloxy-2,4-dioxo-1,3-benzoxazin-3-yl)-propionic acid (formula 1 with $R^1$=COOCH$_3$, $R^2$=H, $R^3$=(CH$_2$)$_2$COOH).

This compound was prepared, analogously to substance 5, from β-alanine and 2,3-di-(methoxycarbonyloxy)-benzoyl chloride in aqueous sodium hydrogen carbonate solution. After recrystallization from ethyl acetate, colorless crystals with a melting point of 140–144° C. were obtained in a yield of 55% of theoretical.

Example 24

Preparation of the sodium salt of N-[3-(8-methoxycarbonyloxy-2,4-dioxo-1,3-benzoxazin-3-yl)-propionyl]-ampicillin (formula 1 with $R^1$=COOCH$_3$, $R^2$=H, $R^3$=(CH$_2$)$_2$CO—N-ampicillino (Na salt)).

(a) Preparation of 3-(8-methoxycarbonyloxy-2,4-dioxo-1,3-benzoxazin-3-yl)-propionyl chloride.

This compound was prepared, analogously to substance 10a, from substance 23 and phosphorus pentachloride in carbon tetrachloride. It was obtained as a yellowish oil in a yield of 100% of theoretical.

(b) Preparation of N-[3-(8-methoxycarbonyloxy-2,4-dioxo-1,3-benzoxazin-3-yl)-propionyl]-ampicillin.

This compound was prepared, analogously to substance 10b, from 2-(8-methoxycarbonyloxy-2,4-dioxo-1,3-benzoxazin-3-yl)-propionyl chloride and the sodium salt of ampicillin. A white powder was obtained in a yield of 88% of theoretical.

(c) Sodium salt.

The salt was prepared, analogously to substance 18, from N-[3-(8-methoxycarbonyloxy-2,4-dioxo-1,3-benzoxazin-3-yl)-propionyl]-ampicillin and sodium 2-ethylhexanoate in ethyl acetate. A white powder was obtained in a yield of 41% of theoretical.

Example 25

Preparation of 3,5-bis-[3-(8-methoxycarbonyloxy-2,4-dioxo-1,3-benzoxazin-3-yl)-propionylamino]-benzoic acid (formula I with $R^1$=COOCH$_3$, $R^2$=H, $R^3$=$R^{18}$ with $R^{10}$, $R^{11}$=H, $R^{12}$=$R^{19}$ in the 3-position, COR$^9$ in the 5-position, $R^9$=OH, $R^{15}$, $R^{14}$=H, n=2, $R^1$, $R^2$ as above).

This compound was prepared, analogously to substance 5, from 3,5-diaminobenzoic acid and 2 molar equivalents of 3-(8-methoxycarbonyloxy-2,4-dioxo-1,3-benzoxazin-3-yl)-propionyl chloride (substance 24a) in aqueous sodium hydrogen carbonate solution. Colorless crystals with a melting point of 160–165° C. were obtained in a yield of 50% of theoretical.

Example 26

Preparation of the sodium salt of N-{3,5-bis-[3-(8-methoxycarbonyloxy-2,4-dioxo-1,3-benzoxazin-3-yl)-propionylamino]-benzoyl}-ampicillin (formula I with $R^1$=COOCH$_3$, $R^2$=H, $R^3$=$R^{18}$ with $R^{10}$, $R^{11}$=H, $R^{12}$=$R^{19}$ in the 3-position, COR$^9$ in the 5-position, $R^9$=N-ampicillino (Na salt), $R^{15}$, $R^{14}$=H, n=2, $R^1$, $R^2$ as above).

(a) Preparation of N-{3,5-bis-[3-(8-methoxycarbonyloxy-2,4-dioxo-1,3-benzoxazin-3-yl)-propionylamino]-benzoyl}-ampicillin.

This compound was prepared, analogously to substance 12, from substance 23 and the sodium salt of ampicillin. A white powder was obtained in a yield of 80% of theoretical.

(b) sodium salt.

This compound was prepared, analogously to substance 18, from N-{3,5-bis-[3-(8-methoxycarbonyloxy-2,4-dioxo-1,3-benzoxazin-3-yl)-propionyl-amino]-benzoyl}-ampicillin and sodium 2-ethylhexanoate in ethyl acetate. A white powder was obtained in a yield of 18% of theoretical.

Example 27

Preparation of 3,5-bis-[(8-methoxycarbonyloxy-2,4-dioxo-1,3-benzoxazin-3-yl)-acetylamino]-benzoic acid (formula I with $R^1$=COOCH$_3$, $R^2$=H, $R^3$=$R^{18}$ with $R^{10}$, $R^{11}$=H, $R^{12}$=$R^{19}$ in the 3-position, COR$^9$ in the 5-position, $R^9$=OH, $R^{15}$, $R^{14}$=H, n=1, $R^1$, $R^2$ as above).

This compound was prepared, analogously to substance 5, from 3,5-diaminobenzoic acid and 2 molar equivalents of (8-methoxycarbonyloxy-2,4-dioxo-1,3-benzoxazin-3-yl)- acetyl chloride (substance 10a) in aqueous sodium hydrogen carbonate solution. After recrystallisation from ethyl acetate, colorless crystals with a melting point of 190–195° C. were obtained in a yield of 53% of theoretical.

Example 28

Preparation of the sodium salt of N-{3,5-bis-[(8-methoxycarbonyloxy-2,4-dioxo-1,3-benzoxazin-3-yl)-acetylamino]-benzoyl}-ampicillin (formula I with $R^1$=COOCH$_3$, $R^2$=H, $R^3$=$R^{18}$ with $R^{10}$, $R^{11}$=H, $R^{12}$=$R^{19}$ in the 3-position, COR$^9$ in the 5-position, $R^9$=N-ampicillino (Na salt), $R^{15}$, $R^{14}$=H, n=1, $R^1$, $R^2$ as above).

(a) Preparation of N-{3,5-bis-(8-methoxycarbonyloxy-2,4-dioxo-1,3-benzoxazin-3-yl)-acetylamino-benzoyl}-ampicillin.

This compound was prepared, analogously to substance 12, from substance 27 and the sodium salt of ampicillin. A white powder was obtained in a yield of 90% of theoretical.

(b) Sodium salt.

The salt was prepared, analogously to substance 18, from N-{3,5-bis-[8-methoxycarbonyloxy-2,4-dioxo-1,3-benzoxazin-3-yl)-acetylamino]-benzoyl}-ampicillin and sodium 2-ethylhexanoate in ethyl acetate. A white powder was obtained in a yield of 17% of theoretical.

Example 29

Preparation of 4-chloro-3-(8-methoxycarbonyloxy-2,4-dioxo-1,3-benzoxazin-3-yl)-benzoic acid (formula I with $R^1$=COOCH$_3$, $R^2$=H, $R^3$=$R^{20}$ with $R^{13}$=Cl in the 2-position, COR$^9$ in the 5-position, $R^9$=OH, p=0).

This compound was prepared, analogously to substance 5, from 3-amino-4-chlorobenzoic acid and 2,3-di-(methoxycarbonyloxy)-benzoyl chloride in aqueous sodium hydrogen carbonate solution. After recrystallization from ethyl acetate, colorless crystals with a melting point of 234–236° C. were obtained in a yield of 41% of theoretical.

Example 30

Preparation of the sodium salt of N-[4-chloro-3-(8-methoxycarbonyloxy-2,4-dioxo-1,3-benzoxazin-3-yl)-benzoyl]-ampicillin (formula I with $R^1$=COOCH$_3$, $R^2$H, $R^3$=$R^{20}$ with $R^{13}$=Cl in the 2-position, COR$^9$ in the 5-position, $R^9$=N-ampicillino (Na salt), p=0).

(a) Preparation of 4-chloro-3-(8-methoxycarbonyloxy-2,4-dioxo-1,3-benzoxazin-3-yl)-benzoyl chloride.

This compound was prepared, analogously to substance 10a, from substance 29 and phosphorus pentachloride in carbon tetrachloride. A yellowish powder with a melting point of 76–78° C. was obtained in a yield of 94% of theoretical.

(b) Preparation of N-[4-chloro-3-(8-methoxycarbonyloxy-2,4-dioxo-1,3-benzoxazin-3-yl)-benzoyl]-ampicillin.

This compound was prepared, analogously to substance 10b, from 4-chloro-3-(8-methoxycarbonyloxy-2,4-dioxo-1,3-benzoxazin-3-yl)-benzoyl chloride and the sodium salt of ampicillin. A white powder was obtained in a yield of 87% of theoretical.

(c) Sodium salt.

The sodium salt was prepared, analogously to substance 18, from N-[4-chloro-3-(8-methoxycarbonyloxy-2,4-dioxo-1,3-benzoxazin-3-yl)-benzoyl]-ampicillinandsodium 2-ethylhexanoate in ethyl acetate. A white powder was obtained in a yield of 55% of theoretical.

Example 31

Preparation of 2-hydroxy-4-(8-methoxycarbonyloxy-2,4-dioxo-1,3-benzoxazin-3-yl)-benzoic acid (formula I with $R^1$=COOCH$_3$, $R^2$=H, $R^3$=$R^{20}$ with $R^{13}$=OH in the 3-position, COR$^9$ in the 4-position, $R^9$=OH, p=0).

This compound was prepared, analogously to substance 5, from 4-aminosalicylic acid and 2,3-di-(methoxycarbonyloxy)-benzoyl chloride in aqueous sodium hydrogen carbonate solution. After recrystallization from ethyl acetate, colorless crystals with a melting point of 261–262° C. were obtained in a yield of 68% of theoretical.

Example 32

Preparation of the sodium salt of N-[2-hydroxy-4-(8-methoxycarbonyloxy-2,4-dioxo-1,3-benzoxazin-3-yl)-benzoyl]-ampicillin (formula I with $R^1$=COOCH$_3$, $R^2$=H, $R^3$=$R^{20}$ with $R^{13}$=OH in the 3-position, COR$^9$ in the 4-position, $R^9$=N-ampicillino (Na salt), p=0).

(a) Preparation of succinimido-2-hydroxy-4-(8-methoxycarbonyloxy-2,4-dioxo-1,3-benzoxazin-3-yl)-benzoate.

A solution of 0.124 g dicyclohexylcarbodiimide in 5 ml anhydrous dioxane was added at 0° C., under an argon atmosphere and with stirring, to a solution of 0.224 g of substance 31 and 0.069 g N-hydroxysuccinimide in 5 ml anhydrous dioxane. The mixture was stirred for 8 hours at 20° C.; the resulting precipitate was filtered out, and the solvent was removed under vacuum. The remaining oil was solidified by triturating with a little isopropanol. Recrystallization from ethyl acetate gave a white powder with a melting point of 145–150° C. in a yield of 0.23 g (81% of theoretical).

(b) Preparation of N-[2-hydroxy-4-(8-methoxycarbonyloxy-2,4-dioxo-1,3-benzoxazin-3-yl)-benzoyl]-ampicillin.

0.191 g ampicillin trihydrate were suspended, under an argon atmosphere, in a mixture of 5 ml tetrahydrofuran and 5 ml water, and were taken into solution by using 138 µl triethylamine. A solution of 0.223 g succinimido-2-hydroxy-4-(8-methoxycarbonyloxy-2,4-dioxo-1,3-benzoxazin-3-yl)-benzoate in 5 ml tetrahydrofuran was then added, with stirring, and the mixture was stirred for 10 hours at 20° C. The reaction mixture was concentrated by evaporation at 20° C. and the residue was treated with water and ethyl acetate. After acidification, the organic phase was separated, washed with a saturated sodium chloride solution and with water, dried over sodium sulfate, and was finally extensively concentrated by evaporation. The ampicillin derivative was precipitated by adding petroleum ether, and was obtained in a yield of 0.28 g (84% of theoretical).

(c) Sodium salt.

The salt was prepared, analogously to substance 18, from N-[2-hydroxy-4-(8-methoxycarbonyloxy-2,4-dioxo-1,3-benzoxazin-3-yl)-benzoyl]-ampicillin and sodium 2-ethylhexanoate in ethyl acetate. A white powder was obtained in a yield of 19% of theoretical.

Example 33

Preparation of 3-(8-methoxycarbonyloxy-2,4-dioxo-1,3-benzoxazin-3-yl)-benzoic acid (formula I with $R^1$=COOCH$_3$, $R^2$=H, $R^3$=$R^{20}$ with $R^{13}$=H, COR$^9$ in the 3-position, $R^9$=OH, p=0).

This compound was prepared, analogously to substance 5, from 3-aminobenzoic acid and 2,3-di-(methoxycarbonyloxy)-benzoyl chloride in aqueous sodium hydrogen carbonate solution. After recrystallization from ethyl acetate, colorless crystals with a melting point of 250–253° C. were obtained in a yield of 71% of theoretical.

Example 34

Preparation of the sodium salt of N-[3-(8-methoxycarbonyloxy-2,4-dioxo-1,3-benzoxazin-3-yl)- benzoyl]-ampicillin (formula I with $R^1$=COOCH$_3$, $R^2$=$R^3$= $R^{20}$ with $R^{13}$=H, COR$^9$ in the 3-position, $R^9$=N-ampicillino (Na-salt), p=0).

(a) Preparation of 3-(8-methoxycarbonyloxy-2,4-dioxo-1, 3-benzoxazin-3-yl)-benzoyl chloride.

This compound was prepared, analogously to substance 10a, from substance 33 and phosphorus pentachloride in carbon tetrachloride. A yellowish oil was obtained in a yield of 97% of theoretical.

(b) Preparation of N-[3-(8-methoxycarbonyloxy-2,4-dioxo-1,3-benzoxazin-3-yl)-benzoyl]-ampicillin.

This compound was prepared, analogously to substance 10b, from 3-(8-methoxycarbonyloxy-2,4-dioxo-1,3-benzoxazin-3-yl)-benzoyl chloride and the sodium salt of ampicillin. A white powder was obtained in a yield of 87% of theoretical.

(c) Sodium salt.

The salt was prepared, analogously to substance 18, from N-[3-(8-methoxycarbonyloxy-2,4-dioxo-1,3-benzoxazin-3-yl)-benzoyl-ampicillin and sodium 2-ethylhexanoate in ethyl acetate. A white powder was obtained in a yield of 59% of theoretical.

Example 35

Preparation of 2L-(8-methoxycarbonyloxy-2,4-dioxo-1,3-benzoxazin-3-yl)-pentanedicarboxylic acid-1-benzyl ester (formula I with $R^1$=COOCH$_3$, $R^2$=H, $R^3$=CHR$^4$—CORP with $R^4$=(CH$_2$)$_2$COOH, $R^1$=O-Benzyl).

1 g L-glutamic acid-1-benzyl ester was dissolved in 40 ml anhydrous tetrahydrofuran under an argon atmosphere. 1.24 ml triethylamine, followed by a solution of 1.22 g 2,3-di-(methoxycarbonyloxy)-benzoyl chloride in 10 ml anhydrous tetrahydrofuran, were added while cooling in ice and stirring. After stirring for 20 hours at 20° C., the tetrahydrofuran was removed under vacuum and the residue was treated with water and ethyl acetate. The mixture was acidified while cooling in ice and stirring, and thereafter the ethyl acetate phase was separated. It was washed repeatedly with water and saturated sodium chloride solution, and was finally concentrated by evaporation. Purification was effected by means of preparative HPLC. A yellowish foam was obtained in a yield of 0.260 g (13% of theoretical).

Example 36

Preparation of the sodium salt of 4-ampicillinocarbamoyl-2L-(8-methoxycarbonyloxy-2,4-dioxo-1,3-benzoxazin-3-yl)-butyric acid benzyl ester (formula I with $R^1$=COOCH$_3$, $R^2$=H, $R^3$=CHR$^4$—COR$^5$ with $R^4$=(CH$_2$)$_2$CO—N-ampicillino (Na salt), $R^5$=O-Benzyl).

(a) Preparation of 4-chlorocarbonyl-2L-(8-methoxycarbonyloxy-2,4-dioxo-1,3-benzoxazin-3-yl)-butyric acid benzyl ester.

This compound was prepared, analogously to substance 10a, from substance 35 and phosphorus pentachloride in carbon tetrachloride. A yellowish oil was obtained in a yield of 97% of theoretical.

(b) Preparation of 4-ampicillinocarbamoyl-2L-(8-methoxycarbonyloxy-2,4-dioxo-1,3-benzoxazin-3-yl)-butyric acid benzyl ester.

This compound was prepared, analogously to substance 10b, from 4-chlorocarbonyl-2L-(8-methoxycarbonyloxy-2, 4-dioxo-1,3-benzoxazin-3-yl)-butyricacid benzyl ester and the sodium salt of ampicillin. A white powder was obtained in a yield of 87% of theoretical.

(c) Sodium salt.

This was prepared, analogously to substance 18, from 4-ampicillino-carbamoyl-2L-(8-methoxycarbonyloxy-2,4-dioxo-1,3-benzoxazin-3-yl)-butanoyl-ampicillin and sodium 2-ethylhexanoate in ethyl acetate. A white powder was obtained in a yield of 46% of theoretical.

Example 37

Preparation of 2L-[2L,6-bis-(8-methoxycarbonyloxy-2,4-dioxo-1,3-benzoxazin-3-yl)-hexanoylamino]-6-(8-methoxycarbonyloxy-2,4-dioxo-1,3-benzoxazin-3-yl)-hexanoic acid (formula I with $R^1$=COOCH$_3$, $R^2$=H, $R^3$=CHR$^4$—COR$^5$ with $R^4$=(CH$_2$)$_4$—Y, $R^5$=$R^{17}$ with X=OH, n=4).

(a) Preparation of 2L-[2L,6-bis-(8-methoxycarbonyloxy-2,4-dioxo-1,3-benzoxazin-3-yl)-hexanoylamino-6-(8-methoxycarbonyloxy-2,4-dioxo-1,3-benzoxazin-3-yl)-hexanoic acid benzyl ester.

1.55 g 6-amino-2-(2,6-diamino-hexanoylamino)-hexanoic acid benzyl ester-tris-p-toluenesulfonate were dissolved in 20 ml anhydrous dimethylformamide under an argon atmosphere and the solution was treated, while cooling in ice and stirring, firstly with 1.48 ml triethylamine and then with a solution of 1.53 g 2,3-di-(methoxycarbonyloxy)-benzoyl chloride in 10 ml anhydrous dimethylformamide. After stirring for 5 hours at 0° C. and 20 hours at 20° C., the dimethylformamide was removed under vacuum and the residue was treated with water and ethyl acetate. The mixture was acidified, while cooling in ice and stirring, and thereafter the ethyl acetate phase was separated. It was washed repeatedly with water and saturated sodium chloride solution and finally concentrated by evaporation. Purification was effected by means of preparative HPLC (elutant: 1/1 acetonitrile/water containing 0.5% trifluoroacetic acid), whereupon 0.25 g of a yellowish oil (14% of theoretical) remained behind.

(b) 0.250 g 2L-[2L,6-bis-(8-methoxycarbonyloxy-2,4-dioxo-1,3-benzoxazin-3-yl)-hexanoylamino]-6-(8-methoxycarbonyloxy-2,4-dioxo-1,3-benzoxazin-3-yl)-hexanoic acid benzyl ester was catalytically hydrogenated in 30 ml ethanol over 0.06 g palladium on activated carbon (10% Pd) at 20° C. and normal pressure. After filtration through celite, the batch was concentrated by evaporation and solidified from ethyl acetate. A yellowish foam was obtained in a yield of 0.220 g (98% of theoretical).

Example 38

Preparation of the sodium salt of N-{2L-[2L,6-Bis-(8-methoxycarbonyloxy-2,4-dioxo-1,3-benzoxazin-3-yl)-hexanoylamino]-6-(8-methoxycarbonyloxy-2,4-dioxo-1,3-benzoxazin-3-yl)-hexanoyl}-ampicillin (formula I with $R^1$=COOCH$_3$, $R^2$=H, $R^3$=CHR$^4$—COR$^5$ with $R^4$=(CH$_2$)$_4$—Y, $R^5$=$R^{17}$ with X=N-ampicillino (Na salt), n=4).

(a) Preparation of N-{2L-[2'L,6'-bis-(8-methoxycarbonyloxy-2,4-dioxo-1,3-benzoxazin-3-yl)-hexanoylamino]-6-(8-methoxycarbonyloxy-2,4-dioxo-1,3-benzoxazin-3-yl)-hexanoyl}-ampicillin.

This compound was prepared, analogously to substance 12, from substance 37 and the sodium salt of ampicillin. A white powder was obtained in a yield of 90% of theoretical.

(b) Sodium salt.

The salt was prepared, analogously to substance 18, from N-{2L-[2L,6-bis-(8-methoxycarbonyloxy-2,4-dioxo-1,3-benzoxazin-3-yl)-hexanoylamino]-6-(8-methoxycarbonyloxy-2,4-dioxo-1,3-benzoxazin-3-yl)-hexanoyl}-ampicillin and sodium 2-ethylhexanoate in ethyl acetate. A white powder was obtained in a yield of 15% of theoretical.

Example 39

Preparation of 3-hydroxy-2L-(8-methoxycarbonyloxy-2,4-dioxo-1,3-benzoxazin-3-yl)-propanoic acid (formula I with $R^1$=COOCH$_3$, $R^2$=H, $R^3$=CHR$^4$—COR$^5$ with $R^4$=CH$_2$—OH, $R^1$=OH).

(a) Preparation of 2L-N-(2,3-dimethoxycarbonyloxybenzoyl)-serine benzyl ester.

This compound was prepared, analogously to substance 35, from L-serine benzyl ester hydrochloride and 2,3-di-(methoxycarbonyloxy)-benzoyl chloride in tetrahydrofuran. A white foam was obtained in a yield of 43% of theoretical.

(b) 1.3 g 2L-N-(2,3-dimethoxycarbonyloxybenzoyl)-serine benzyl ester were suspended in 50 ml ethanol and 300 mg of a palladium-carbon catalyst (10%) were added. After conversion in a hydrogen atmosphere, the mixture was shaken for 2 hours at 20° C. and normal pressure. After filtration through celite, it was concentrated by evaporation. Purification by means of preparative HPLC gave a white foam. Yield: 599 mg (48% of theoretical).

Example 40
Preparation of the sodium salt of N-[3-hydroxy-2L-(8-methoxy-carbonyloxy-2,4-dioxo-1,3-benzoxazin-3-yl)-propionyl]-ampicillin (formula I with $R^1$=COOCH$_3$, $R^2$=H, $R^3$=CHR$^4$—COR$^5$ with $R^4$=CH$_2$—OH, $R^5$=N-ampicillino (Na salt).

(a) Preparation of N-[3-hydroxy-2L-(8-methoxycarbonyloxy-2,4-dioxo-1,3-benzoxazin-3-yl)-propionyl]-ampicillin.

This compound was prepared, analogously to substance 12, from substance 39 and the sodium salt of ampicillin. A white powder was obtained in a yield of 90% of theoretical.

(b) Sodium salt.

The sodium salt was prepared, analogously to substance 18, from N-[3-hydroxy-2L-(8-methoxycarbonyloxy-2,4-dioxo-1,3-benzoxazin-3-yl)-propionyl]-ampicillin and sodium 2-ethylhexanoate in ethyl acetate. A white powder was obtained in a yield of 10% of theoretical.

Example 41
Preparation of (8-ethoxycarbonyloxy-2,4-dioxo-1,3-benzoxazin-3-yl)-acetic acid (formula I with $R^1$=COOC$_2$H$_5$, $R^2$=H, $R^3$=CH$_2$COOH).

This compound was prepared, analogously to substance 1, from glycine and 2,3-di-(ethoxycarbonyloxy)-benzoyl chloride in aqueous sodium hydrogen carbonate solution. After recrystallization from ethyl acetate, colorless crystals with a melting point of 162–163° C. were obtained in a yield of 69% of theoretical.

Example 42
Preparation of N-{N'-[6-(8-methoxycarbonyloxy-2,4-dioxo-1,3-benzoxazin-3-yl)-hexyl]-N'-[2,3-di-(methoxycarbonyloxy)-benzoyl]-6-aminohexyl}-N-[2,3-di-(methoxycarbonyloxy)-benzoyl]-glycine (formula I with $R^3$=Z—CHR$^4$—COR$^5$; $R^1$, $R^7$=COOCH$_3$; $R^2$, $R^4$, $R^6$=H; $R^5$=OH; n=6; m=2).

(a) Preparation of the benzyl ester ($R^5$=OCH$_2$C$_6$H$_5$).

A solution of 864 mg 2,3-di-(methoxycarbonyloxy)-benzoyl chloride in 5 ml dichloromethane was added at –30° C. to a solution of 880 mg N-[N'-(6-aminohexyl)-6-aminohexyl-glycine benzyl ester tosylate and 1.04 ml tri-ethylamine in 20 ml dichloromethane. The mixture was stirred for 1 hour at –10° C. and for 1 hour at room temperature, and was then filtered. The solution was concentrated by evaporation, and the residue was taken up in 20 ml ethyl acetate. The ethyl acetate solution was washed three times, with 1 M hydrochloric acid, saturated sodium bicarbonate solution and with water each time. After drying and distilling off the solvent under vacuum, a colorless solid was obtained in a yield of 650 mg (60% of theoretical).

(b) Preparation of the acid ($R^5$=OH).

The above benzyl ester was hydrogenated in methanol with 100 mg Pd/C (10%), for 3 hours in a shaking apparatus at room temperature. After filtering out the catalyst through celite, the solvent was distilled off under vacuum. A colorless solid was obtained in a yield of 70% of theoretical.

In the examples, HPLC denotes high performance liquid chromatography.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

TABLE 2

Antibacterial activity of benzoxazinedione-antibiotic conjugates.
MIC values (mg/ml)

| Substance | Pseudomonas aeruginosa SG 137 | Pseudomonas aeruginosa ATCC 27853 | NCTC 10662 | Kleb-siella ATCC 10031 | E. coli ATCC 25922 | Stenotrop. maltoph. GN 12873 | Staphylococcus SG 511 |
|---|---|---|---|---|---|---|---|
| azlocillin | 3.12 | 3.12 | 6.25 | 6.25 | 6.25 | 12.5 | 0.2 |
| ampicillin | >100 | >100 | >100 | 25 | 6.25 | >100 | <0.05 |
| substance 10 | 0.78 | 6.25 | 3.12 | 0.2 | 6.25 | 3.12 | 0.78 |
| substance 11 | 0.78 | 3.12 | 3.12 | | 12.5 | 12.5 | 0.78 |
| substance 12 | 0.4 | 3.12 | 1.56 | 6.25 | 3.12 | 1.56 | 0.78 |
| substance 13 | 0.2 | 1.56 | 3.12 | 0.1 | 3.12 | 3.12 | 1.56 |
| substance 14 | 1.56 | 3.12 | 1.56 | 0.78 | 3.12 | 1.56 | 1.56 |
| substance 15 | 0.78 | 1.56 | 1.56 | 3.12 | 12.5 | 6.25 | 1.56 |
| substance 18 | 0.4 | 1.56 | 1.56 | 6.25 | 25 | 3.12 | 1.56 |
| substance 20 | 1.56 | 6.25 | 12.5 | 6.25 | 12.5 | 6.25 | 0.78 |
| substance 22 | 0.2 | 1.56 | 0.78 | 6.25 | 25 | 0.78 | 25 |
| substance 24 | 3.12 | 6.25 | 12.5 | 50 | 25 | 25 | 12.5 |
| substance 26 | 0.05 | 0.2 | 0.1 | 0.2 | 6.25 | 1.56 | 6.25 |
| substance 28 | 0.05 | 1.56 | 1.56 | 1.56 | 25 | 3.12 | 25 |
| substance 30 | <0.05 | 0.78 | 0.4 | 1.56 | 6.25 | 0.78 | 1.56 |
| substance 32 | 0.1 | 0.78 | 0.78 | 3.12 | 50 | 0.78 | 0.4 |
| substance 34 | <0.05 | 0.2 | 0.4 | 1.56 | 3.12 | 1.56 | 0.78 |
| substance 36 | 0.2 | 0.78 | 1.56 | 1.56 | 3.12 | 1.56 | 0.2 |
| substance 38 | 0.2 | 0.78 | 0.78 | 0.4 | 6.25 | 0.4 | 3.12 |
| substance 40 | 0.4 | 1.56 | 1.56 | 25 | 12.5 | 3.12 | 0.4 |

What is claimed is:

1. A benzoxazinedione compound corresponding to formula I:

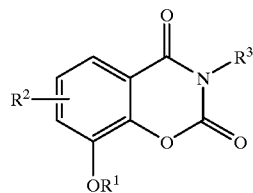

wherein
R¹ represents H, CO—$C_{1-8}$alkyl or COO—$C_{1-8}$alkyl;
R² represents H, $C_{1-8}$alkyl or halogen, and
R³ is selected from the following groups a) through f):
  a) —Z—CHR⁴—COR⁵, wherein
    Z is a group corresponding to the formula

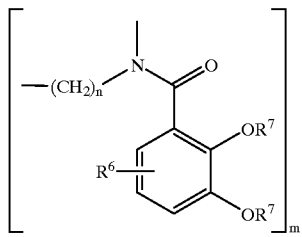

in which
  R⁶ represents H, $C_{1-8}$alkyl or halogen;
  R⁷ represents H, CO—$C_{1-6}$alkyl or COO—$C_{1-6}$alkyl;
  n is an integer from 1 to 10, and
  m is 1 or 2;
R⁴ represents H; $C_{1-8}$alkyl; phenyl; phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; a group —$(CH_2)_n$COX, or a group —$(CH_2)_n$—Y, wherein n has the meaning given above;
X represents
  OA, wherein A represents H, $C_{1-8}$alkyl, benzyl, an alkali metal ion, an ammonium ion or a substituted ammonium ion; or
  an active ingredient residue which is bonded via an OH or an NH group; and
Y represents a benzoxazinedione residue which may be the same or different from the benzoxazinedione residue in formula I and which corresponds to the formula

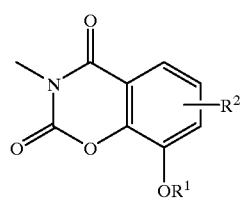

wherein R¹ and R² have the meanings given above; and R⁵ represents
  OA, wherein A has the meaning given above, or an active ingredient residue which is bonded via an OH or an NH group, or
  a —NH—CHR⁸—COR⁹ group, wherein R⁸ represents H; $C_{1-8}$alkyl; phenyl or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; and
R⁹ represents OA, wherein A is as defined above, or an active ingredient residue which is bonded via an OH or an NH group; or
a group corresponding to the formula

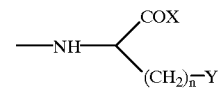

wherein n, X and Y have the meanings given above;
b) —CHR⁴—COR⁵, wherein R⁴ and R⁵ have the meanings given above;
c) a group corresponding to the formula

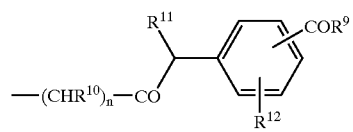

wherein
  COR⁹ and R¹² may be in any possible positions;
  n and R⁹ have the meanings given above;
  R¹⁰ and R¹¹ are independently selected from H; $C_{1-8}$alkyl; phenyl; or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; and
  R¹² represents H, $C_{1-8}$alkyl, halogen, hydroxy, $C_{1-8}$alkoxy, a group Y as defined above, or a group corresponding to formula

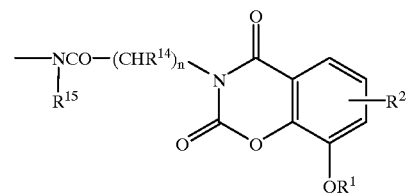

wherein
  n, R¹ and R² have the meanings given above, and R¹⁴ and R¹⁵ have the meanings given for R¹ and R², respectively;
d) a group corresponding to the formula:

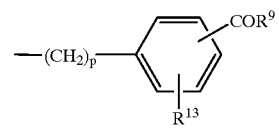

wherein
  COR⁹ and R¹³ may be in any possible positions;
  R⁹ has the meaning given above;
  R¹³ represents H, $C_{1-8}$alkyl, halogen, hydroxy, $C_{1-8}$alkoxy or a group Y as defined above, and p is an integer from 0 to 2;

e) a group corresponding to one of the formulas

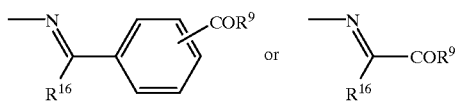

wherein $R^9$ has the meaning given above, and $R^{16}$ represents H; $C_{1-8}$alkyl; phenyl; or phenyl substituted by $C_{1-8}$alkyl, $C_{1-8}$alkoxy, hydroxy, carboxy, phenyl, halogen, amino, $C_{1-5}$alkylamino, di-C$_{1-5}$alkylamino, halogen substituted Cl$_{1-8}$alkyl, Cl$_{1-5}$alkoxycarbonyl, or $C_{1-5}$-acyloxy;

f) an active ingredient residue which is bonded via an OH group or an NH group; or an ester of a compound of formula I in which $R^3$ contains a free carboxyl group, which ester is cleavable under physiological conditions.

2. A compound according to claim 1, wherein X is a residue of an antibiotic which is bonded via an OH or an NH group.

3. A compound according to claim 1, wherein $R^5$ is a residue of an antibiotic which is bonded via an OH or an NH group.

4. A compound according to claim 1, wherein $R^9$ is a residue of an antibiotic which is bonded via an OH or an NH group.

5. A compound according to claim 1, wherein $R^3$ is a residue of an antibiotic which is bonded via an OH group or an NH group.

6. A compound according to claim 1, wherein $R^1$ is carboxyalkyl, $R^2$ is H, $R^3$ is CHR$^4$—COR$^5$, $R^4$ is H. $C_{1-8}$ straight or branched alkyl, phenyl or p-hydroxyphenyl, and $R^5$ is OH.

7. A compound according to claim 1, wherein $R^1$ is carboxyalkyl, $R^2$ is H, $R^3$ is CH$_2$CONHCHR$^8$COOH, and $R^8$ is H, $C_{1-5}$ straight or branched alkyl, phenyl, or phenyl substituted by $C_{1-5}$ straight or branched alkyl, halogen, $C_{1-5}$ straight or branched alkoxy, hydroxy, carboxy, $C_{1-5}$ straight or branched alkoxycarbonyl, or halogen-substituted $C_{1-5}$ straight or branched alkyl.

8. (8-methoxycarbonyloxy-2,4-dioxobenzoxazin-3-yl)-acetic acid according to claim 1.

9. (8-methoxycarbonyloxy-2,4-dioxobenzoxazin-3-yl)-acetyl-glycine according to claim 1.

10. A compound according to claim 1, wherein X or $R^3$ or $R^5$ or $R^9$ denotes a residue of an antibacterial active ingredient.

11. A compound according to claim 1, wherein X or $R^3$ or $R^5$ or $R^9$ is a residue of a cephalosporin which is bonded via an NH or OH group.

12. A compound according to claim 1, wherein X or $R^3$ or $R^5$ or $R^9$ is a residue of a penicillin which is bonded via an NH or OH group.

13. A compound according to claims 1, wherein X or $R^3$ or $R^5$ or $R^9$ is an ampicillin residue.

14. A compounds according to claim 1, wherein X or $R^3$ or $R^5$ or $R^9$ denotes an amoxicillin or O-acylamoxicillin residue.

15. A compound according to claim 1, wherein X or $R^3$ or $R^5$ or $R^9$ denotes a 6-aminopenicillanic acid residue.

16. A compound according to claim 1, wherein X or $R^3$ or $R^5$ or $R^9$ is a tetracycline residue which is bonded via an NH or an OH group.

17. A compound according to claim 1, wherein X or $R^3$ or $R^5$ or $R^9$ is a residue of a macrolide which is bonded via an NH or an OH group.

18. A compound according to claim 1, wherein X or $R^3$ or $R^5$ or $R^9$ is a residue of a quinolone which is bonded via an NH or an OH group.

19. A compound according to claim 1, wherein X or $R^3$ or $R^5$ or $R^9$ is a residue of a carbapenem which is bonded via an NH or an OH group.

20. N-(8-methoxycarbonyloxy-2,4-dioxobenzoxazin-3-yl-acetyl)-ampicillin according to claim 1.

21. N-(8-methoxycarbonyloxy-2,4-dioxobenzoxazin-3-yl-acetyl)-amoxicillin according to claim 1.

22. A pharmaceutical composition comprising a compound according to claim 1 and at least one pharmaceutical carrier or adjuvant.

23. A method of promoting bacterial growth comprising the step of culturing bacteria in a culture medium comprising an effective bacterial growth promoting amount of a benzoxazinedione compound corresponding to formula I:

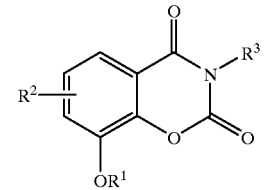

wherein $R^1$ represents H, CO—$C_{1-8}$alkyl or COO—$C_{1-8}$alkyl;

$R^2$ represents H, $C_{1-8}$ alkyl or halogen, and $R^3$ is selected from the following groups a) through f):

a) —Z—CHR$^4$—COR$^5$, wherein

Z is a group corresponding to the formula

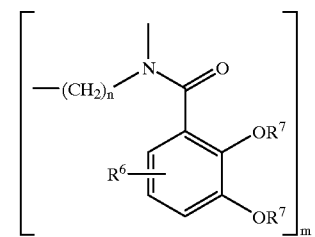

in which 3

$R^6$ represents H, $C_{1-8}$alkyl or halogen;

$R^7$ represents H, CO—$C_{1-6}$alkyl or COO—$C_{1-6}$alkyl;

n is an integer from 1 to 10, and m is 1 or 2;

$R^4$ represents H; $C_{1-8}$alkyl; phenyl; phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; a group —(CH$_2$)$_n$COX, or a group —(CH$_2$)$_n$—Y, wherein n has the meaning given above;

X represents

OA, wherein A represents H, $C_{1-8}$alkyl, benzyl, an alkali metal ion, an ammonium ion or a substituted ammonium ion; or an active ingredient residue which is bonded via an OH or an NH group; and Y represents a benzoxazinedione residue which may be the same or different from the benzoxazinedione residue in formula I and which corresponds to the formula

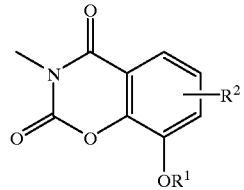

wherein $R^1$ and $R^2$ have the meanings given above; and $R^5$ represents

OA, wherein A has the meaning given above, or an active ingredient residue which is bonded via an OH or an NH group, or a —NH—CHR$^8$—COR$^9$ group, wherein $R^8$ represents H; $C_{1-8}$alkyl; phenyl or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; and $R^9$ represents OA, wherein A is as defined above, or an active ingredient residue which is bonded via an OH or an NH group; or a group corresponding to the formula

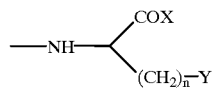

wherein n, X and Y have the meanings given above;

b) —CHR$^4$—COR$^5$, wherein $R^4$ and $R^5$ have the meanings given above;

c) a group corresponding to the formula

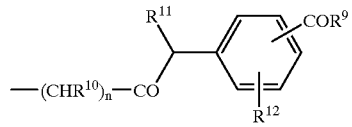

wherein

COR$^9$ and $R^{12}$ may be in any possible positions;

n and $R^9$ have the meanings given above;

$R^{10}$ and $R^{11}$ are independently selected from H; $C_{1-8}$alkyl; phenyl; or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy; and $R^{12}$ represents H, $C_{1-8}$alkyl, halogen, hydroxy, $C_{1-8}$alkoxy, a group Y as defined above, or a group corresponding to formula

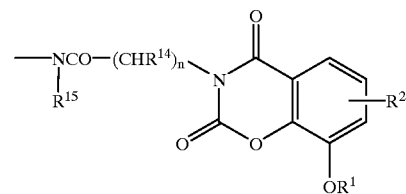

wherein n, $R^1$ and $R^2$ have the meanings given above, and $R^{14}$ and $R^{15}$ have the meanings given for $R^1$ and $R^2$, respectively;

d) a group corresponding to the formula:

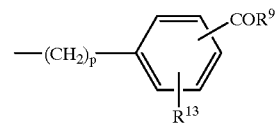

wherein

COR$^9$ and $R^{13}$ may be in any possible positions;

$R^9$ has the meaning given above;

$R^{13}$ represents H, $C_{1-8}$alkyl, halogen, hydroxy, $C_{1-8}$alkoxy or a group Y as defined above, and p is an integer from 0 to 2;

e) a group corresponding to one of the formulas

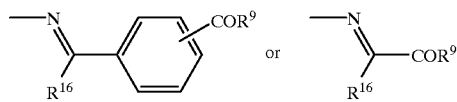

wherein $R^9$ has the meaning given above, and $R^{16}$ represents H; $C_{1-8}$alkyl; phenyl; or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy;

f) an active ingredient residue which is bonded via an OH group or an NH group; or an ester of a compound of formula I in which $R^3$ contains a free carboxyl group, which ester is cleavable under physiological conditions.

24. A method of treating a bacterial infection in a patient comprising the step of administering to said patient an effective anti-bacterial amount of a benzoxazinedione compound corresponding to formula I:

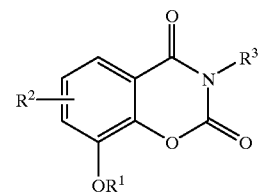

wherein OR $R^1$ represents H, CO—$C_{1-8}$alkyl or COO—$C_{1-8}$alkyl;

$R^2$ represents H, $C_{1-8}$alkyl or halogen, and $R^3$ is selected from the following groups a) through f):

a) —Z—CHR$^4$—COR$^5$, wherein

Z is a group corresponding to the formula

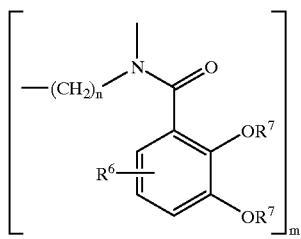

in which

R$^6$ represents H, C$_{1-8}$alkyl or halogen;

R$^7$ represents H, CO—C$_{1-6}$alkyl or COO—C$_{1-6}$alkyl;

n is an integer from 1 to 10, and m is 1 or 2;

R$^4$ represents H; C$_{1-8}$alkyl; phenyl; phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$alkyl, C$_{1-5}$alkoxycarbonyl, or C$_{1-5}$acyloxy; a group —(CH$_2$)$_n$COX, or a group —(CH$_2$)$_n$—Y, wherein n has the meaning given above;

X represents

OA, wherein A represents H, C$_{1-8}$alkyl, benzyl, an alkali metal ion, an ammonium ion or a substituted ammonium ion; or an active ingredient residue which is bonded via an OH or an NH group; and Y represents a benzoxazinedione residue which may be the same or different from the benzoxazinedione residue in formula I and which corresponds to the formula

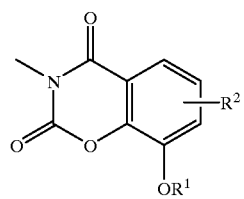

wherein R$^1$ and R$^2$ have the meanings given above; and R$^5$ represents

OA, wherein A has the meaning given above, or an active ingredient residue which is bonded via an OH or an NH group, or a —NH—CHR$^8$—COR$^9$ group, wherein R$^8$ represents H; C$_{1-8}$alkyl; phenyl or phenyl substituted by C$_{1-8}$alkyl, C$_{1-8}$alkoxy, hydroxy, carboxy, phenyl, halogen, amino, C$_{1-5}$alkylamino, di-C$_{1-5}$akylamino, halogen substituted C$_{1-8}$alkyl, C$_{1-5}$alkoxycarbonyl, or C$_{1-5}$acyloxy; and R$^9$ represents OA, wherein A is as defined above, or an active ingredient residue which is bonded via an OH or an NH group; or a group corresponding to the formula

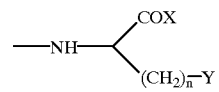

wherein n, X and Y have the meanings given above;

b) —CHR$^4$—COR$^5$, wherein R$^4$ and R$^5$ have the meanings given above;

c) a group corresponding to the formula

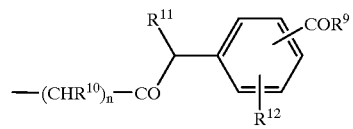

wherein

COR$^9$ and R$^{12}$ may be in any possible positions;

n and R$^9$ have the meanings given above;

R$^{10}$ and R$^{11}$ are independently selected from H; C$_{1-8}$alkyl; phenyl; or phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$alkyl, C$_{1-5}$alkoxycarbonyl, or C$_{1-5}$acyloxy; and R$^{12}$ represents H, C$_{1-8}$alkyl, halogen, hydroxy, C$_{1-8}$alkoxy, a group Y as defined above, or a group corresponding to formula

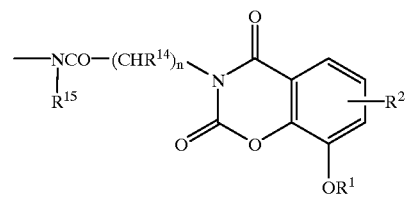

wherein n, R$^1$ and R$^2$ have the meanings given above, and

R$^{14}$ and R$^{15}$ have the meanings given for R$^1$ and R$^2$ respectively;

d) a group corresponding to the formula:

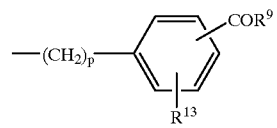

wherein

COR$^9$ and R$^{13}$ may be in any possible positions;

R$^9$ has the meaning given above;

R$^{13}$ represents H, C$_{1-8}$alkyl, halogen, hydroxy, C$_{1-8}$alkoxy or a group Y as defined above, and p is an integer from 0 to 2;

e) a group corresponding to one of the formulas

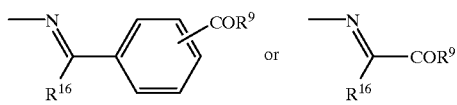

wherein
R$^9$ has the meaning given above, and
R$^{16}$ represents H; C$_{1-8}$alkyl; phenyl; or phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$alkyl, C$_{1-5}$alkoxycarbonyl, or C$_{1-5}$acyloxy;

f) an active ingredient residue which is bonded via an OH group or an NH group; or an ester of a compound of formula I in which R$^3$ contains a free carboxyl group, which ester is cleavable under physiological conditions;

and wherein X or R$^3$ or R$^5$ or R$^9$ is a residue of an anti-bacterial active agent.

25. A method of treating an iron metabolism disorder in a patient comprising the step of administering to said patient an effective iron metabolism regulating amount of a benzoxazinedione compound corresponding to formula I:

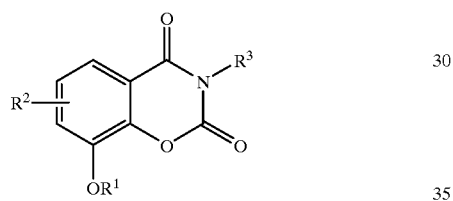

wherein
R$^1$ represents H, CO—C$_{1-8}$alkyl or COO—C$_{1-8}$alkyl;
R$^2$ represents H, C$_{1-8}$alkyl or halogen, and
R$^3$ is selected from the following groups a) through f):
  a) —Z—CHR$^4$—COR$^5$, wherein
    Z is a group corresponding to the formula

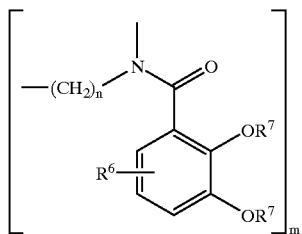

in which
R$^6$ represents H, C$_{1-8}$alkyl or halogen;
R$^7$ represents H, CO—C$_{1-6}$alkyl or COO—C$_{1-6}$alkyl;
n is an integer from 1 to 10, and
m is 1 or 2;
R$^4$ represents H; C$_{1-8}$alkyl; phenyl; phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$alkyl, C$_{1-5}$alkoxycarbonyl, or C$_{1-5}$acyloxy; a group —(CH$_2$)$_n$COX, or a group —(CH$_2$)$_n$—Y, wherein n has the meaning given above;

X represents
  OA, wherein A represents H, C$_{1-8}$alkyl, benzyl, an alkali metal ion, an ammonium ion or a substituted ammonium ion; or
  an active ingredient residue which is bonded via an OH or an NH group; and
Y represents a benzoxazinedione residue which may be the same or different from the benzoxazinedione residue in formula I and which corresponds to the formula

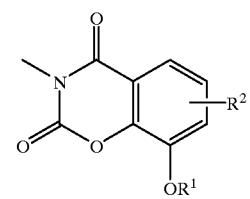

wherein R$^1$ and R$^2$ have the meanings given above; and R$^5$ represents
OA, wherein A has the meaning given above, or
an active ingredient residue which is bonded via an OH or an NH group, or
a —NH—CHR$^8$—COR$^9$ group, wherein
  R$^8$ represents H; C$_{1-8}$alkyl; phenyl or phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$-alkyl, C$_{1-5}$alkoxycarbonyl, or C$_{1-5}$acyloxy; and
  R$^9$ represents OA, wherein A is as defined above, or an active ingredient residue which is bonded via an OH or an NH group; or
a group corresponding to the formula

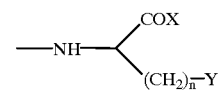

wherein n, X and Y have the meanings given above;
b) —CHR$^4$—COR$^5$, wherein R$^4$ and R$^5$ have the meanings given above;
c) a group corresponding to the formula

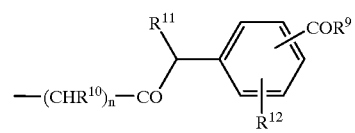

wherein
COR$^9$ and R$^{12}$ may be in any possible positions;
n and R$^9$ have the meanings given above;
R$^{10}$ and R$^{11}$ are independently selected from H; C$_{1-8}$alkyl; phenyl; or phenyl substituted by C$_{1-8}$alkyl, C$_{1-8}$alkoxy, hydroxy, carboxy, phenyl, halogen, amino, C$_{1-5}$alkylamino, di-C$_{1-5}$alkylamino, halogen substituted C$_{1-8}$alkyl, C$_{1-5}$alkoxycarbonyl, or C$_{1-5}$acyloxy; and
R$^{12}$ represents H, C$_{1-8}$alkyl, halogen, hydroxy, C$_{1-8}$alkoxy, a group Y as defined above, or a group corresponding to formula

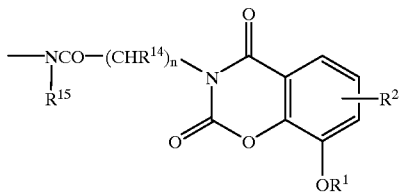

wherein
n, $R^1$ and $R^2$ have the meanings given above, and $R^{14}$ and $R^{15}$ have the meanings given for $R^1$ and $R^2$, respectively;

d) a group corresponding to the formula:

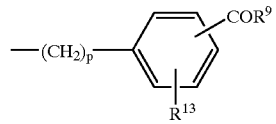

wherein
COR$^9$ and $R^{13}$ may be in any possible positions;
$R^9$ has the meaning given above;
$R^{13}$ represents H, $C_{1-8}$alkyl, halogen, hydroxy, $C_{1-8}$alkoxy or a group Y as defined above, and p is an integer from 0 to 2;

e) a group corresponding to one of the formulas

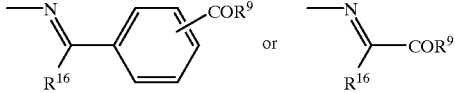

wherein
$R^9$ has the meaning given above, and
$R^{16}$ represents H; $C_{1-8}$alkyl; phenyl; or phenyl substituted by $C_{1-8}$alkyl, $C_{1-8}$alkoxy, hydroxy, carboxy, phenyl, halogen, amino, $C_{1-5}$alkylamino, di-$C_{1-5}$alkylamino, halogen substituted $C_{1-8}$alkyl, $C_{1-5}$alkoxycarbonyl, or $C_{1-5}$acyloxy;

f) an active ingredient residue which is bonded via an OH group or an NH group; or an ester of a compound of formula I in which $R^3$ contains a free carboxyl group, which ester is cleavable under physiological conditions;

and wherein X or $R^3$ or $R^5$ or $R^9$ is a residue of an iron chelating agent.

* * * * *